United States Patent
Logan et al.

(10) Patent No.: US 9,526,541 B2
(45) Date of Patent: *Dec. 27, 2016

(54) FLEXIBLE INTRAMEDULLARY ROD

(71) Applicant: Howmedica Osteonics Corp., Mahwah, NJ (US)

(72) Inventors: Scott Logan, Mahwah, NJ (US); Kirby Hitt, Temple, TX (US)

(73) Assignee: Howmedica Osteonics Corp., Mahwah, NJ (US)

( * ) Notice: Subject to any disclaimer, the term of this patent is extended or adjusted under 35 U.S.C. 154(b) by 24 days.

This patent is subject to a terminal disclaimer.

(21) Appl. No.: 14/533,738

(22) Filed: Nov. 5, 2014

(65) Prior Publication Data

US 2015/0057661 A1 Feb. 26, 2015

Related U.S. Application Data

(60) Continuation of application No. 12/766,114, filed on Apr. 23, 2010, now Pat. No. 8,900,233, which is a
(Continued)

(51) Int. Cl.
*A61B 17/56* (2006.01)
*A61B 17/72* (2006.01)
(Continued)

(52) U.S. Cl.
CPC ......... *A61B 17/7208* (2013.01); *A61B 17/921* (2013.01); *A61B 17/1675* (2013.01)

(58) Field of Classification Search
CPC . A61B 17/72; A61B 17/7208; A61B 17/7216; A61B 17/7225; A61B 17/7233; A61B 17/7241; A61B 17/725; A61B 17/7283; A61B 17/7291; A61B 17/744; A61B 17/748; A61B 17/842; A61B 17/846; A61B 17/848; A61B 17/1725; A61B 17/921; A61B 17/1717
See application file for complete search history.

(56) References Cited

U.S. PATENT DOCUMENTS

| 4,135,507 A | 1/1979 | Harris |
| 4,446,857 A * | 5/1984 | Otte ................... A61B 17/7283 606/62 |

(Continued)

FOREIGN PATENT DOCUMENTS

| EP | 0 355 411 A1 | 2/1990 |
| FR | 2288506 A1 | 5/1976 |

(Continued)

OTHER PUBLICATIONS

Karzenis, et al., 'Access to the medullary canal in closed antegrade femoral nailing: a technical report.' Archives of Orthopaedic and Trauma, Apr. 2003, p. 1; abstract; para [Introduction and Technique].
(Continued)

*Primary Examiner* — Lynnsy Summitt
(74) *Attorney, Agent, or Firm* — Lerner, David, Littenberg, Krumholz & Mentlik, LLP

(57) ABSTRACT

An elongated rod for insertion into a bowed canal of a bone such as a femoral medulla of a femur bone, wherein the canal is bowed in one plane. The rod has a longitudinal axis disposed on a first plane and one or more cutouts formed in at least a portion of a length of the rod and on opposite sides of the first plane. The rod is flexible along a second plane which is co-planar with the bowed canal plane and which is disposed on the longitudinal axis and perpendicular to the first plane.

29 Claims, 18 Drawing Sheets

Related U.S. Application Data division of application No. 11/803,336, filed on May 14, 2007, now abandoned.

(51) Int. Cl.
*A61B 17/92* (2006.01)
*A61B 17/16* (2006.01)

(56) References Cited

U.S. PATENT DOCUMENTS

| | | | |
|---|---|---|---|
| 4,791,919 A | 12/1988 | Elloy et al. | |
| 4,808,186 A | 2/1989 | Smith | |
| 4,825,857 A | 5/1989 | Kenna | |
| 4,851,008 A | 7/1989 | Johnson | |
| 4,907,578 A | 3/1990 | Petersen | |
| 4,921,501 A | 5/1990 | Giacometti et al. | |
| 5,041,114 A | 8/1991 | Chapman et al. | |
| 5,053,035 A | 10/1991 | McLaren | |
| 5,122,134 A | 6/1992 | Borzone et al. | |
| 5,135,527 A | 8/1992 | Ender | |
| 5,234,433 A | 8/1993 | Bert et al. | |
| 5,336,265 A | 8/1994 | Serbousek et al. | |
| 5,374,235 A | 12/1994 | Ahrens | |
| 5,514,140 A | 5/1996 | Lackey | |
| 5,562,674 A | 10/1996 | Stalcup et al. | |
| 5,618,286 A * | 4/1997 | Brinker | A61B 17/72 606/60 |
| 5,776,204 A | 7/1998 | Noble et al. | |
| 5,830,216 A | 11/1998 | Insall et al. | |
| 5,879,352 A | 3/1999 | Filoso et al. | |
| 6,168,595 B1 | 1/2001 | Durham et al. | |
| 6,193,723 B1 | 2/2001 | Cripe et al. | |
| 6,205,411 B1 | 3/2001 | DiGioia, III et al. | |
| 6,322,591 B1 | 11/2001 | Ahrens | |
| 6,337,142 B2 | 1/2002 | Harder et al. | |
| 6,416,517 B2 | 7/2002 | Harder et al. | |
| 6,454,810 B1 * | 9/2002 | Lob | A61B 17/72 606/62 |
| 6,547,791 B1 * | 4/2003 | Buhren | A61B 17/7208 606/62 |
| 6,740,092 B2 | 5/2004 | Lombardo et al. | |
| 6,949,101 B2 | 9/2005 | McCleary et al. | |
| 7,008,425 B2 | 3/2006 | Phillips | |
| 7,237,556 B2 | 7/2007 | Smothers et al. | |
| 2002/0107522 A1 | 8/2002 | Picard et al. | |
| 2003/0069581 A1 | 4/2003 | Stinson et al. | |
| 2004/0106923 A1 | 6/2004 | Swanson | |
| 2005/0055028 A1 * | 3/2005 | Haines | A61B 17/155 606/79 |
| 2005/0216007 A1 | 9/2005 | Woll et al. | |
| 2005/0273102 A1 | 12/2005 | Powell et al. | |
| 2006/0264950 A1 | 11/2006 | Nelson et al. | |
| 2006/0264952 A1 * | 11/2006 | Nelson | A61B 17/7208 606/916 |
| 2007/0123878 A1 | 5/2007 | Shaver et al. | |

FOREIGN PATENT DOCUMENTS

| | | |
|---|---|---|
| GB | 2232355 A | 12/1990 |
| WO | 2005094705 A2 | 10/2005 |
| WO | 2005096976 A1 | 10/2005 |
| WO | 2006124764 A1 | 11/2006 |

OTHER PUBLICATIONS

International Search Report for Application No. PCT/US2008/06143 dated Sep. 29, 2008.
Extended European Search Report for Application No. EP08754440 dated Apr. 19, 2013.

\* cited by examiner

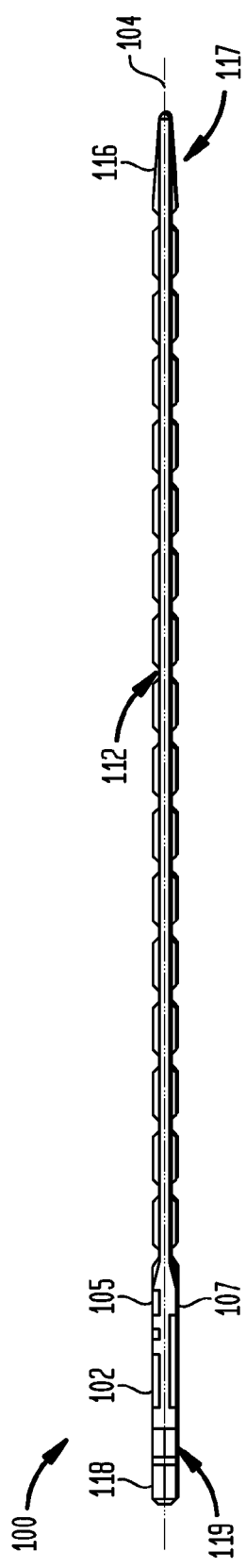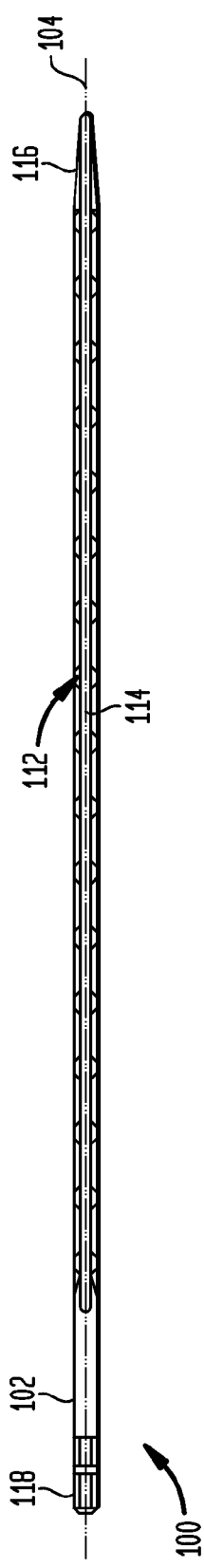

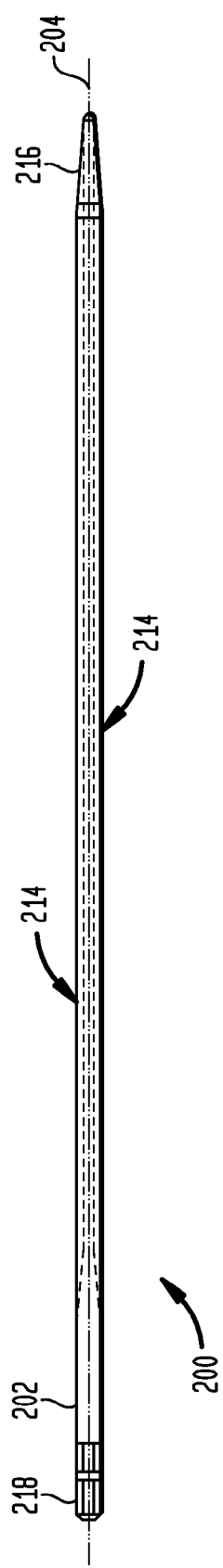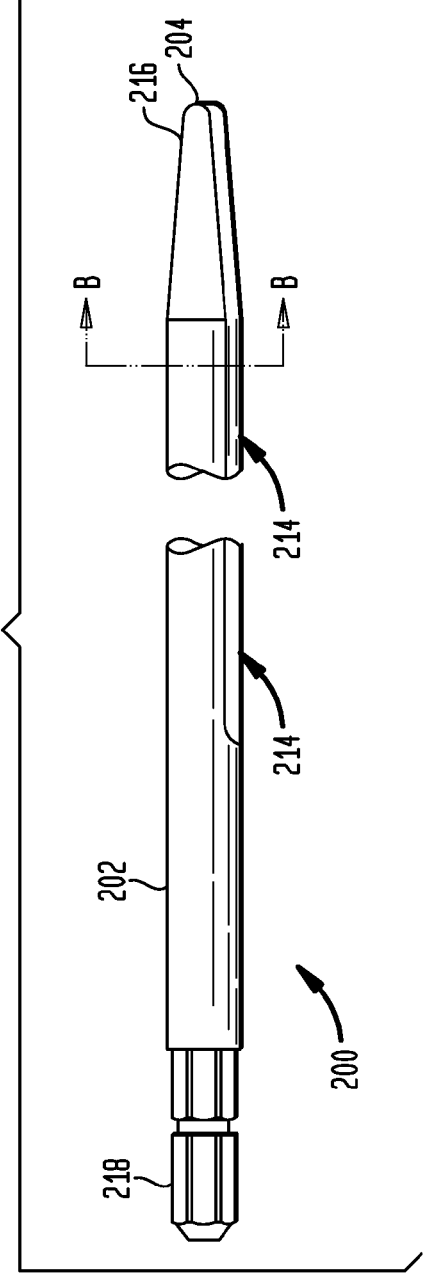

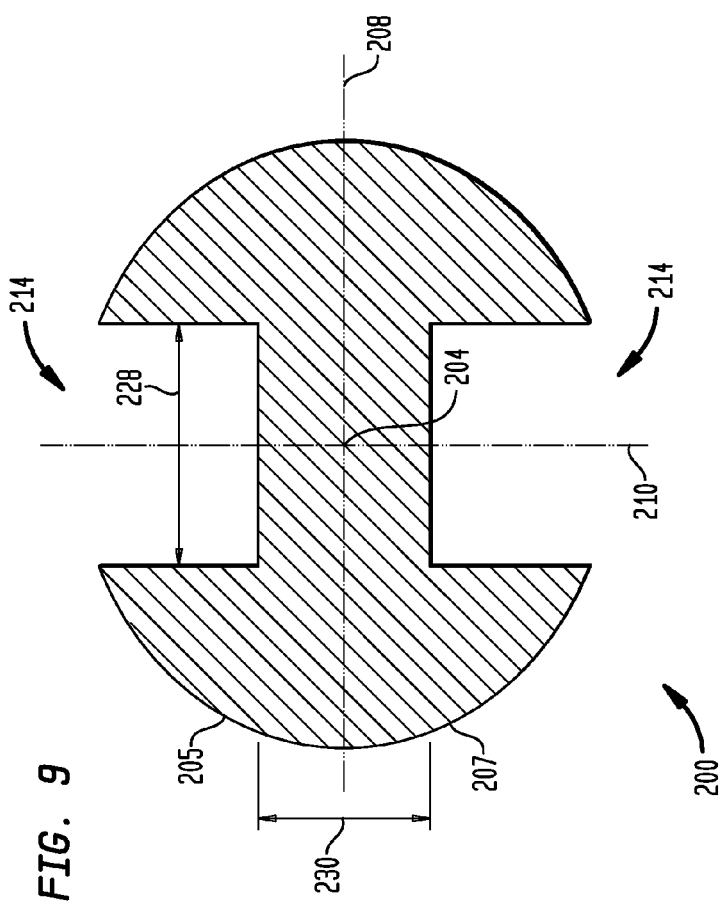
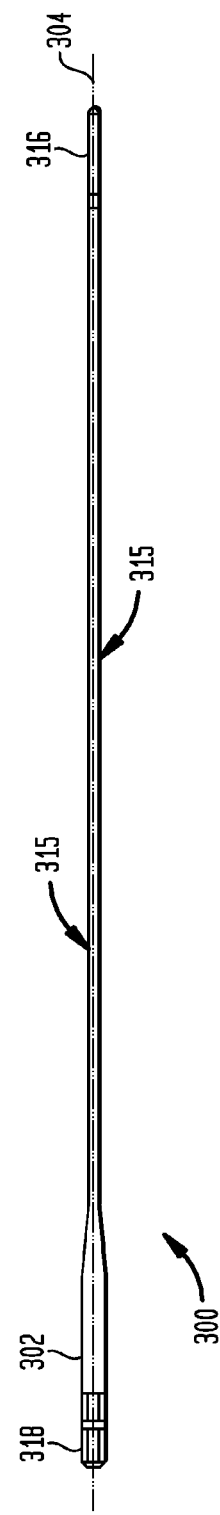
FIG. 9
FIG. 10

FLEXIBLE INTRAMEDULLARY ROD

CROSS-REFERENCE TO RELATED APPLICATIONS

The present application is a continuation of U.S. patent application Ser. No. 12/766,114, filed Apr. 23, 2010, now U.S. Pat. No. 8,900,233, which is a divisional of U.S. patent application Ser. No. 11/803,336, filed May 14, 2007, now abandoned, the disclosures of which are incorporated herein by reference.

BACKGROUND OF THE INVENTION

Joint replacement surgery (arthroplasty) is often performed on the knee. In a total knee arthroplasty (TKA), the diseased cartilage surfaces of the thighbone (femur), the shinbone (tibia) and the kneecap (patella) are replaced by prosthetic components. Most of the other structures of the knee, such as the connecting ligaments, remain intact. This surgical procedure requires alignment of the femoral and tibial components to a vertical or mechanical axis of the limb. The procedure also requires enlarging the canal in the femur called a femoral medulla as well as enlarging the canal in the tibia called the tibial medulla. When the femoral and tibia bones are fully extended (i.e., the knee joint is in extension), a proximal-distal axis drawn through the center of a femoral head (proximal femur) passes through the knee joint in a healthy knee and along the tibial canal to the ankle joint. This proximal-distal axis is called the mechanical axis, and it is along this axis that a load is transmitted. However, the axis of the femoral medulla may lie at an angle of up to 7 degrees to this mechanical axis along the coronal plane. The femoral medulla has an anterior bow along a plane parallel to the sagittal plane. The bow represents a concavity facing in the posterior direction and serves to increase the space for lodgment of the soft tissue masses during knee flexion. Knee flexion refers to rotation of the femur with respect to the tibia. As part of a surgical procedure to replace the distal femur, a surgical device called an intramedullary (IM) rod is inserted into the femoral medulla. A cutting block is then mounted onto the rod and placed against the distal portion of the femur. The cutting block provides cutting guide surfaces for making the required cuts on the distal femur such as distal, posterior, anterior, posterior chamfer and anterior chamfer cuts. It is important that the rod provide an accurate reference for the cutting block.

SUMMARY OF THE INVENTION

The present application provides an improved intramedullary (IM) rod. The rod of the present application includes cutouts which allow the rod to flex along a plane parallel to the sagittal plane but remain relatively rigid along the coronal plane. Thus the rod is adapted to conform to the natural anatomical bow along a plane parallel to the sagittal plane of the femoral medulla. This feature provides proper orientation of the cutting block which improves the accuracy of cuts such as the distal cut of the distal femur. This provides the proper orientation of a femoral component such as a replacement knee and thus an improved knee replacement surgical procedure.

In one aspect of the present application, disclosed is a surgical instrument for insertion into a canal bowed in one plane. The surgical instrument has a longitudinal axis disposed on a first plane and one or more cutouts formed in at least a portion of a length of the rod and on opposite sides of the first plane. The rod is flexible along a second plane which is co-planar with the bowed canal plane and which is disposed on the longitudinal axis and perpendicular to the first plane.

In one or more embodiments, the elongated rod may be generally solid and the rod may be substantially rigid along the first plane. The rod may be capable of resiliently flexing along the second plane in a range from a radius of about 0 to degrees to 9 degrees. The cutouts may include one or more grooves extending along at least a portion of the longitudinal axis and on opposite sides of the first plane. The cutouts may have a generally flat shape extending along at least a portion of the longitudinal axis and on opposite sides of the first plane. The cutouts may have a generally semi-circular cross-sectional shape along the second plane. The rod may have a first end adapted for insertion into the canal of a bone and a second end adapted for attachment to a tool to support the rod.

In another aspect of the present application, disclosed is a method of using a surgical instrument using the rod as described above. In yet another aspect of the present application, disclosed is a surgical instrument kit that includes a rod as described above and a tool adapted to attach to the rod.

BRIEF DESCRIPTION OF THE DRAWINGS

FIG. 1 shows an elevational view of a rod in accordance with an embodiment of the present application.

FIG. 2 shows a cutaway, top view of the rod of FIG. 1.

FIG. 7 shows a side view of a rod in accordance with another embodiment of the present application.

FIG. 8 shows an enlarged view showing the cutouts of the rod of FIG. 7.

FIG. 9 shows a cross-sectional view taken along section line B-B of the rod of FIG. 8.

FIG. 10 shows a side view of a rod in accordance with yet another embodiment of the present application.

DETAILED DESCRIPTION

Figure 3:
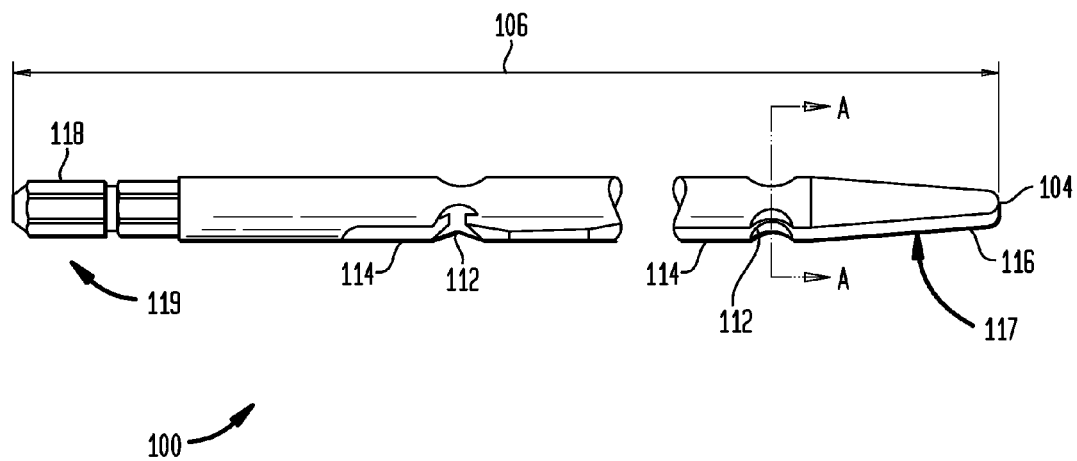
FIG. 3 shows a cutaway, close up view of the rod of FIG. 1.
Figure 4:
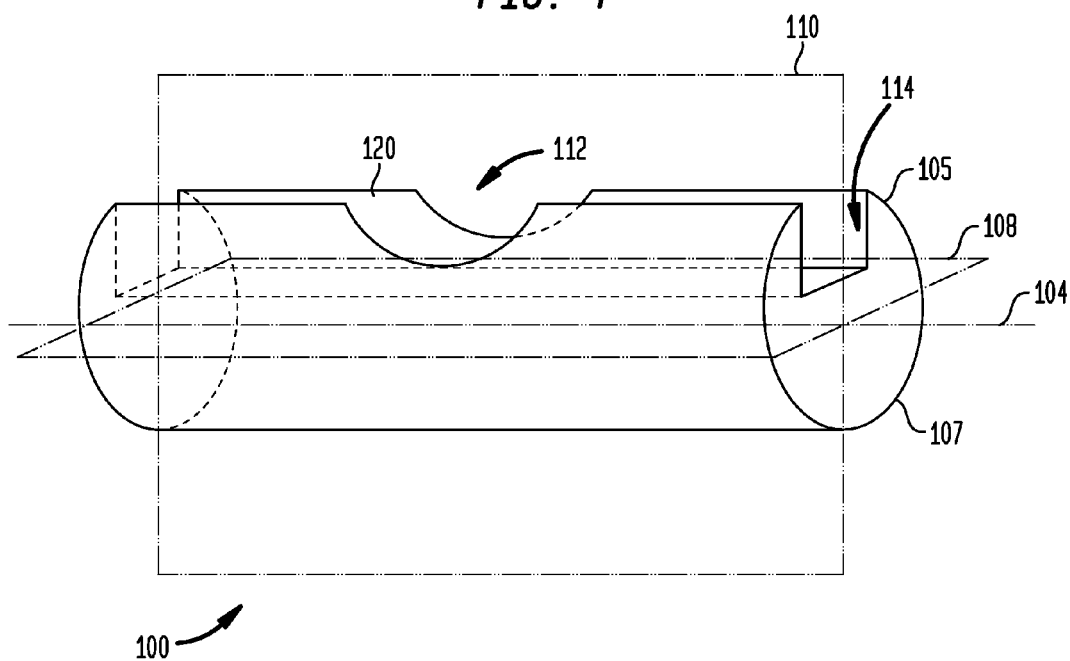
FIG. 4 shows an enlarged view showing the cutouts of the rod of FIG. 1.
Figure 5:
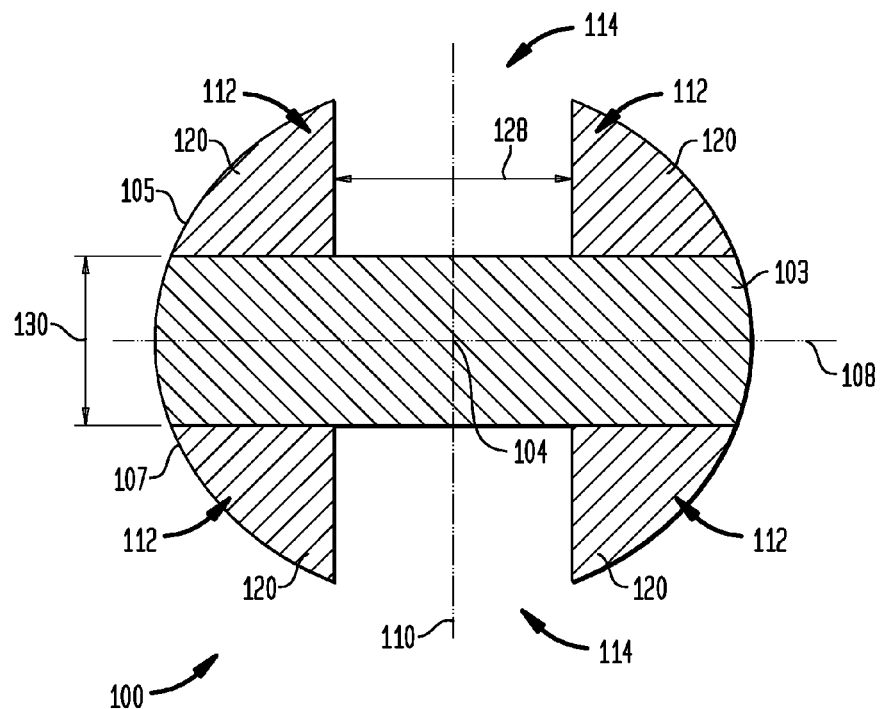
FIG. 5 shows a cross-sectional view taken along section line A-A of the rod of FIG. 3.
Figure 6:
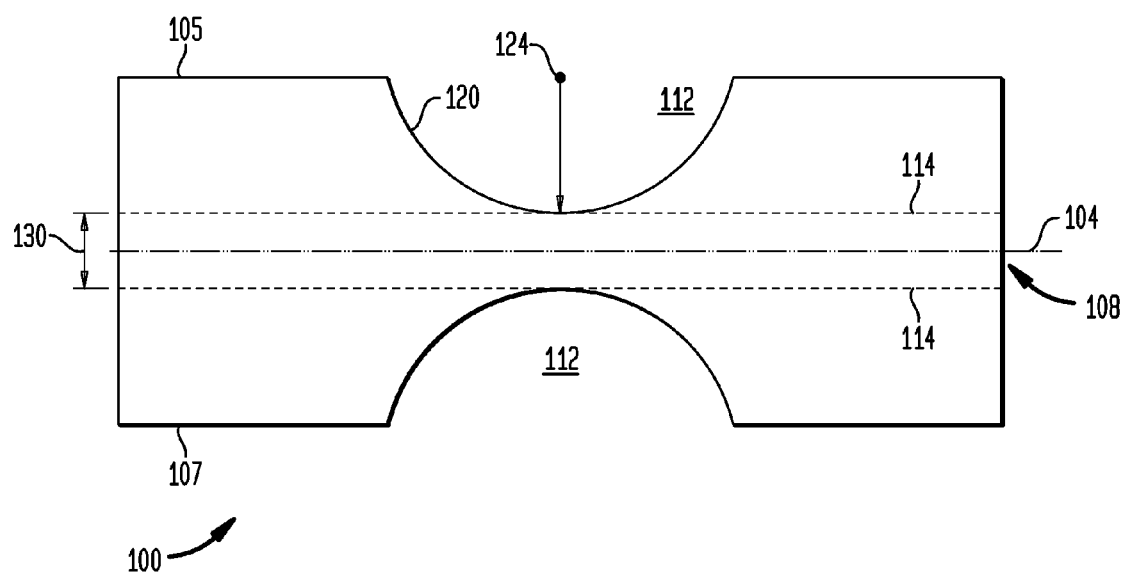
FIG. 6 shows a detailed view of a portion of the rod of FIG. 3.

FIGS. 1-6 show a surgical instrument 100 in accordance with an embodiment of the present application. The surgical instrument comprises an intramedullary (IM) rod 100 having an elongated rod body 102 for insertion into the femoral medulla for alignment purposes during a surgical procedure such as total knee arthroplasty (TKA). The rod body 102 has a longitudinal axis 104 extending through the center of the rod body and extending along the length 106 of the rod body. The longitudinal axis 104 is disposed on a first plane 108 and a second plane 110 which is perpendicular to the first plane. One or more first cutouts 112 and second cutouts 114 are formed in at least a portion of the length 106 of the rod and symmetrically on opposite sides 105, 107 of the first plane 108. The cutouts 112, 114 may permit the rod 100 to be resiliently flexible along the second plane 110 and substantially rigid along the first plane 108.

In one embodiment, the rod 100 is configured for insertion into a bowed canal of bone such as the femoral medulla of the femur bone of a human body. The first plane 108 corresponds to a frontal or coronal plane that separates a human body into anterior and posterior parts. The second plane 110 corresponds to a plane parallel to the sagittal plane which separates a human body into left and right side parts. The top side 105 of the rod corresponds to the anterior side or ventral side corresponding to the side closer to the anterior surface of the body. The bottom side 107 of the rod corresponds to the posterior or dorsal side corresponding to the side closer to the posterior surface of the body. In one embodiment, the femoral medulla bows or bends along a plane parallel to the sagittal plane along an axis but remains relatively straight along the coronal plane. The rod is configured for insertion into the femoral medulla and for bending or conforming to the bowing of the femoral medulla along a plane parallel to the sagittal plane and for remaining substantially rigid along the coronal plane, as explained in further detail below.

The rod body 102 has an insertion portion 117 at a first end 116 adapted for insertion into the femoral medulla through an opening at the base of the femur. In one embodiment, the insertion portion 117 is tapered with the narrow portion extending away from the rod. An attachment portion 119 at a second end 118 of the rod is adapted for attachment to a tool (not shown) to support the rod and to urge the rod into the femoral medulla. In one embodiment, the attachment portion 119 has a generally hexagonal cross-sectional shape for attachment to a matching recess of a tool. The rod body 102 can be composed of stainless steel, titanium, a biocompatible material, or a combination thereof. The rod body 102 can be a solid rod or have a hollow center.

The first cutouts 112 are shown as having a generally semi-circular shape and a concave surface 120 about the second plane. However, other shapes are contemplated such as triangular shapes and other surfaces such as uneven surfaces. The cutouts 112 have a radius 124 of about 0.095 inches. The cutouts 112 are spaced apart from each other along the longitudinal axis 104 by a distance of about 0.750 inches between the centers of the cutouts. The cutouts 112 are spaced apart from each other about both sides of the second plane 110 by a distance 130 of about 0.10 inches. The second cutouts 114 are shown as grooves having a generally square cross-sectional shape along the longitudinal axis 104. However, it is contemplated that second cutouts 114 can have other shapes such as a triangular cross-sectional shape. The second cutouts 114 extend along the longitudinal axis 104 and at least a portion of the length of the rod body 102. The cutouts 114 have a width of about 0.125 inches shown by arrow 128. The length 106 of the rod body 102 is about 16 inches but the rod can have a length in the range from about 11 to 16 inches. The rod body 102 has a diameter of about 5/16 (0.0625) inches and a central core thickness 130 of about 0.100 inches. Other diameters are contemplated such as ¼" or ⅜". It will be appreciated that other sizes, shapes and configurations are contemplated.

FIGS. 7-9 show a surgical instrument comprising an IM rod 200 having an elongated rod body 202 in accordance with another embodiment of the present application. The rod 200 is similar to the rod 100 of FIGS. 1-6 in that both rods are configured for insertion into the femoral medulla. For example, the rod body 202 has a longitudinal axis 204 through the center of the rod and extending along the length of the rod. The longitudinal axis 204 is disposed on a first plane 208 and a second plane 210 which is perpendicular to the first plane. The rod body 202 has a first end 216 adapted for insertion into the femoral medulla and a second end 218 adapted for attachment to a tool.

However, the rod body 202 has cutouts 214 formed at least on a portion of the length of the rod and symmetrically on opposite sides 205, 207 of the first plane 208, unlike the combination of cutouts 112, 114 of rod 102 of FIGS. 1-2. However, like the cutouts 112, 114 of rod 102, the cutouts 214 also permit the rod 202 to be resiliently flexible along the second plane 210 and substantially rigid along the first plane 208. The shape of the cutouts 214 is similar to those of the cutouts 114 of FIGS. 1-6. For example, the cutouts 114 are grooves having a generally square cross-sectional shape along the longitudinal axis 204. The cutouts 214 have a width 228 of about 0.125 inches and a central core thickness 230 of about 0.100 inches. The other characteristics of the rod 200 are similar to those of rod 100 and are not repeated for simplicity.

Figure 11:
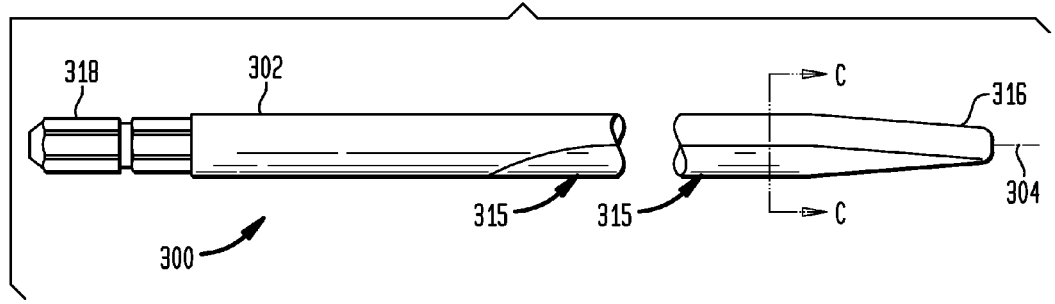
FIG. 11 shows an enlarged view showing the cutouts of the rod of FIG. 10.
Figure 12:
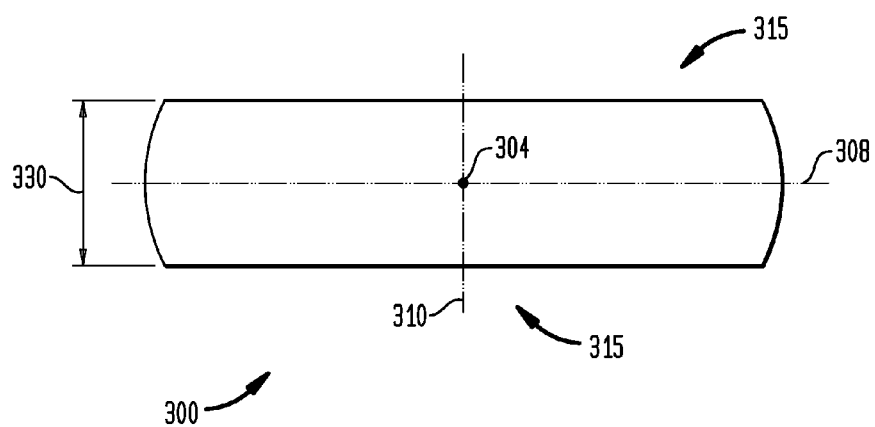
FIG. 12 shows a cross-sectional view taken along section line C-C of the rod of FIG. 11.
Figure 13:
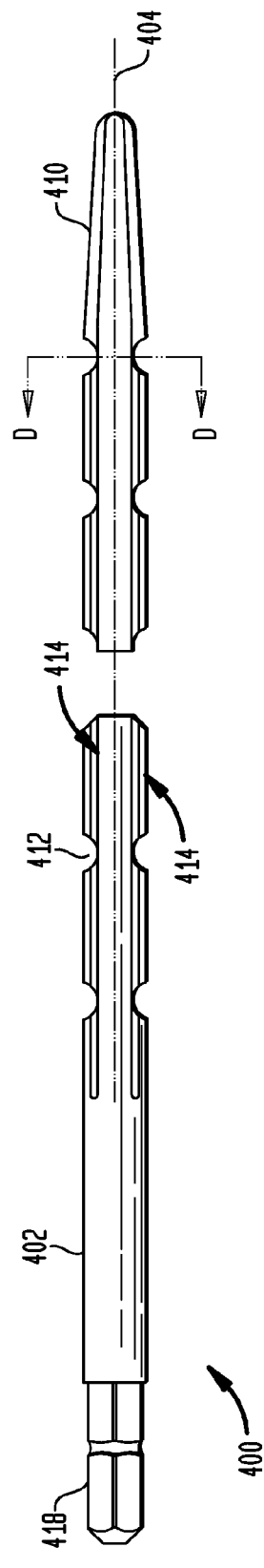
FIG. 13 shows a side view of a rod in accordance with another embodiment of the present application.
Figure 14:
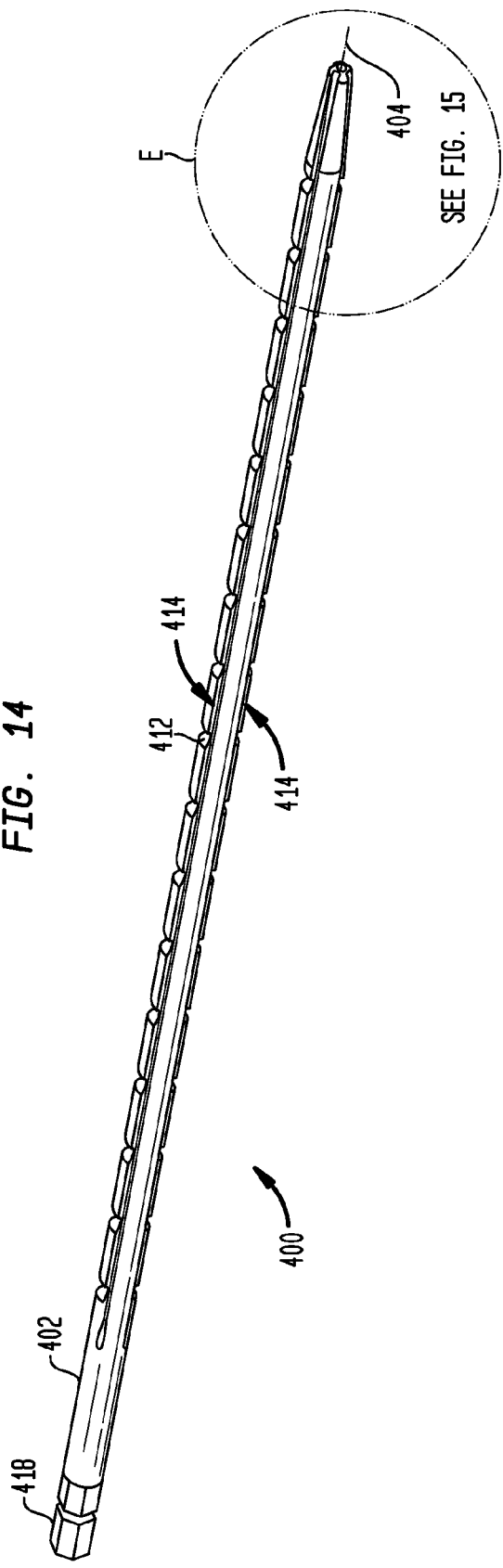
FIG. 14 shows a perspective view of the rod of FIG. 13.
Figure 15:
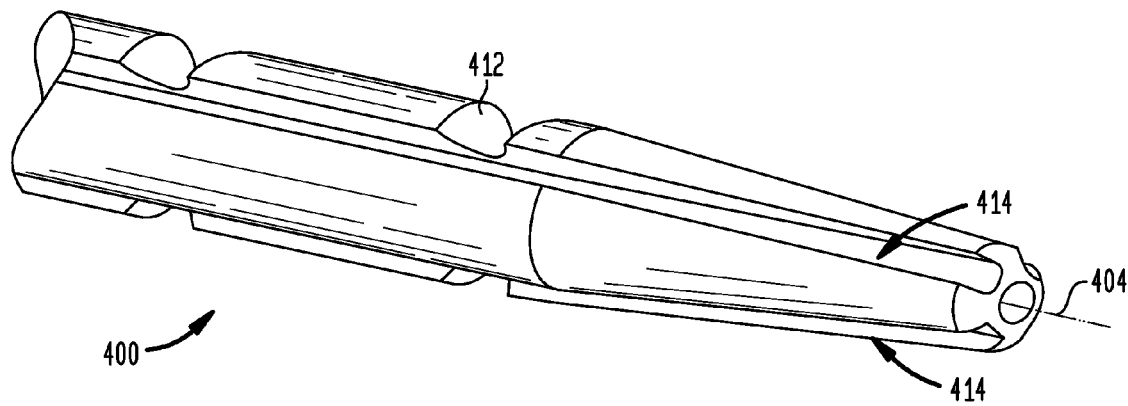
FIG. 15 shows a detailed view of a leading portion E of the rod of FIG. 14.
Figure 16:
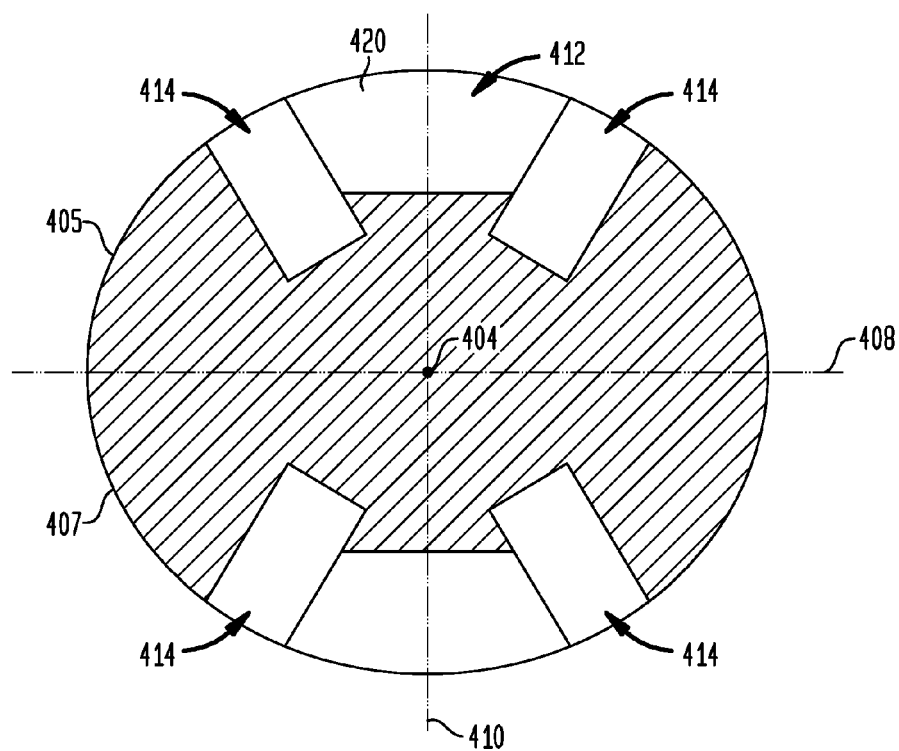
FIG. 16 shows a cross-sectional view taken along section line D-D of the rod of FIG. 13.

FIGS. 10-12 show a surgical instrument comprising a rod 300 having an elongated rod body 302 in accordance with another embodiment of the present application. The rod 300 is similar to the rod 100 of FIGS. 1-6 in that both rods are configured for insertion into the femoral medulla. For example the rod 302 has a longitudinal axis 304 which is disposed on a first plane 308 and a second plane 310 which is perpendicular to the first plane. The rod 302 has a first end 316 and a second end 318. However, the rod 302 only has cutouts 315 formed in at least a portion of the length of the rod and symmetrically on opposite sides 305, 307 of the first plane 308, unlike the combination of cutouts 112, 114 of the rod 102 of FIGS. 1-2. However, like the cutouts 112, 114 of rod 102, the cutouts 315 also permit the rod 302 to be resiliently flexible along the second plane 310 and substantially rigid along the first plane 308. However, the shape of the cutouts 315 is different than that of the cutouts 112, 114 of FIGS. 1-6. For example, the cutouts 315 form flat surfaces along the longitudinal axis 304 and extend at least a portion of the length of the rod 302. The rod 302 has a central core thickness 330 of about 0.100 inches. The other characteristics of the rod 300 are similar to those of rod 100 and are not repeated for simplicity.

FIGS. 13-16 show a surgical instrument 400 having an elongated rod body 402 in accordance with another embodiment of the present application. The rod 400 is similar to the rod 100 of FIGS. 1-6 in that both rods are configured for insertion into the femoral medulla. For example, the rod body 402 has a longitudinal axis 404 through the center of the rod body and extending along the length of the rod body. The longitudinal axis 404 is disposed on a first plane 408 and a second plane 410 which is perpendicular to the first plane. The rod body 402 has a first end 416 adapted for insertion into the femoral medulla and a second end 418 adapted for attachment to a tool.

The rod body 402 includes first cutouts 412 formed at least on a portion of the length of the rod and symmetrically on opposite sides 405, 407 of the first plane 408, like the cutouts 112 of rod 102 of FIGS. 1-2. However, the rod body 402 includes two cutouts 414 on opposite sides 405, 407 of the first plane, unlike a single cutout 114 of rod body of FIGS. 1-6. For example, the cutouts 412 have a semicircular shape with a curved surface 420. In addition, the two cutouts 414 are offset from each other by an angle, such as 45 degrees from a center of the cutouts, unlike the cutout 114 of the rod body 102 which has a base side that is parallel to the first plane. However, like the cutouts 112, 114 of the rod body 102, the cutouts 412, 414 of the rod body 402 also permit the rod body 402 to be resiliently flexible along the second plane 410 and substantially rigid along the first plane 408. The shape of the cutouts 412, 414 is similar to that of the cutouts 112, 114 of the rod of FIGS. 1-6 and is not described further for simplicity. The other characteristics of the rod 400 are similar to those of rod 100 and are not repeated for simplicity.

The rods of the present application can be made using well known metalworking techniques. For example, in one embodiment, a metal working lathe can be used to form the cutouts of the rods. The lathe can use computer controlled techniques, such as computer numerically controlled (CNC) features, for increased accuracy and mass production of the rods. The lathe can be connected to a bar feeder mechanism to efficiently handle the rods including loading the rods onto the lathe. The lathe can also employ "live" tooling techniques to produce the various forms of cutouts of the rods. For example, the live tooling techniques can produce the semi-circular type cutouts 112 and the groove type cutouts 114 of the rod of FIG. 1.

Figure 17:
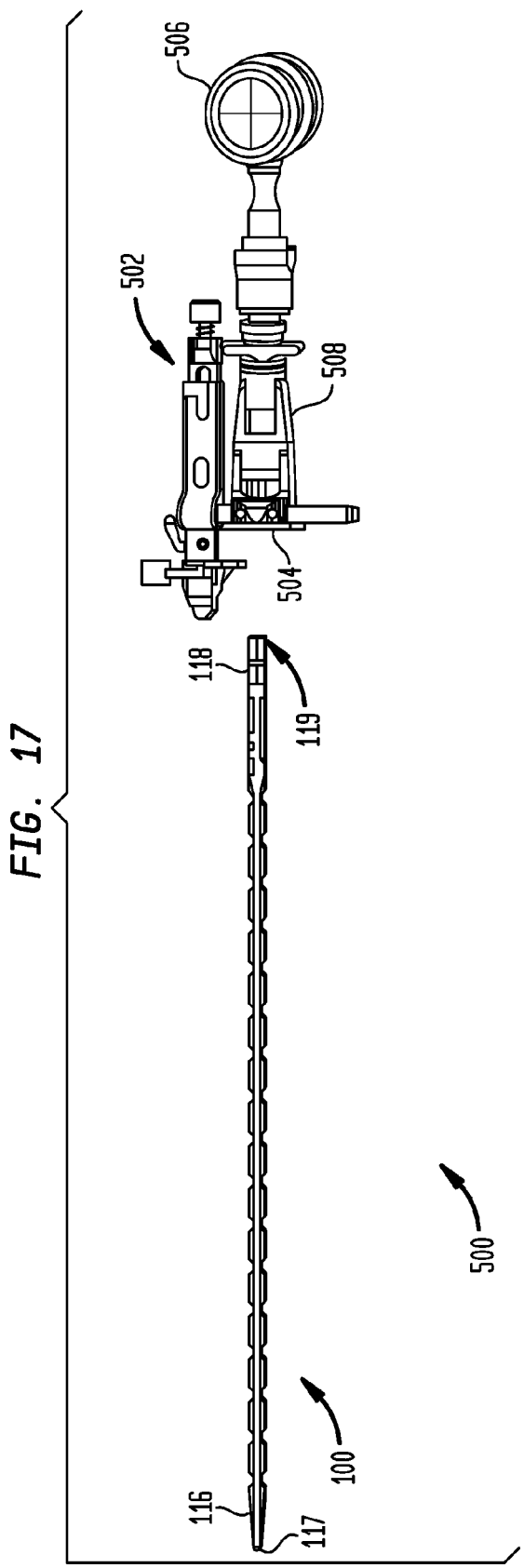
FIG. 17 shows a surgical kit in accordance with an embodiment of the present application.

FIG. 17 shows a surgical instrument kit 500 in accordance with an embodiment of the present application. The kit 500 comprises a tool 502, known as an "introducer", capable of supporting a rod of the present invention, such as rod 100 of FIGS. 1-6. The tool 502 has an attachment portion 504 for attachment to the attachment portion 119 at the distal end 118 of the rod 100. In one embodiment, the attachment portion 504 can be adapted to receive the attachment portion 119 of the rod 100 to provide a detachable locking mechanism. For example, the attachment portion 504 of the tool 502 can include a recess with a hexagonal shape and the attachment portion 119 of the rod 100 can have a hexagonal shape that is complementary to the shape of the attachment portion 504 of the rod. In another embodiment, the attachment portion 119 of the rod 100 can be indexed with the attachment portion 504 of the tool to ensure proper alignment of the rod with the tool. This feature also may help ensure that the rod is properly aligned in the femoral medulla.

The tool 502 can also have a handle 506 for gripping the tool, rotating the rod, or for other purposes. In one embodiment, the handle 506 can rotate about its central axis to rotate the attached rod. In one embodiment, the tool 502 includes a femoral alignment guide 508 coupled between the rod 100 and the handle 506. As explained below, the femoral alignment guide 508 helps align the rod 100 with respect to the femoral medulla of a femur.

FIGS. 18-28 show portions of a surgical procedure that include using the rod 100 of FIGS. 1-6 in accordance with an embodiment of the present application. It should be understood that any of the other rods of the present application can be used. In one example, the surgical procedure includes total knee arthroplasty (TKA) of the knee (i.e., knee replacement) which involves the resection of portions of the femur and tibia using a cutting block and attachment a knee prosthesis to the resected area. Alignment of the cutting block with respect to the femur is critical to the procedure. As explained below in detail, the rod and the techniques for using the rod of the present application may help improve such alignment. As explained below, the surgical procedure involves, generally, forming an entrance hole and a femoral medulla in the distal femur, inserting and aligning the rod in the femoral medulla, attaching a cutting block to the rod to make cuts to the distal femur, and mounting the femoral components to the prepared distal femur.

Figure 18:
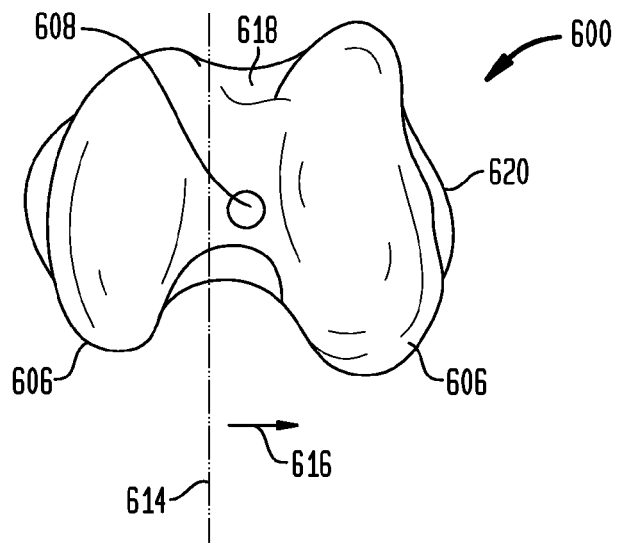
FIG. 18 shows a view of a distal femur of a femur bone in preparation for having an entrance hole formed thereon for a surgical procedure in accordance with an embodiment of the present application.

Referring to FIG. 18, shown is a first step in the surgical procedure which includes forming an entrance hole 608 in a distal femur 620 of a femur bone 600. This includes locating the position of the entrance hole 608 in the distal femur. In one embodiment, the entrance hole can be located between condyles 606 and an intercondylar notch 618 of the distal femur 620. In one embodiment, the entrance hole can be located as close as possible to a posterior cruciate ligament (PCL) (not shown). In another embodiment, the entrance hole can be located slightly medial, in the direction shown by arrow 616, to a midline axis 614 of the distal femur. Although not shown, other steps can be performed in preparation for forming the entrance hole 608. For example, the tibia (not shown) can be resected and the patellar (not shown) can be everted to provide space for the formation of the entrance hole as well as the femoral medulla. In addition, the identification of landmarks to help locate the position of the entrance hole can be aided by the removal of osteophytes (not shown) from the margins of the intercondylar notch 618.

Figure 19:
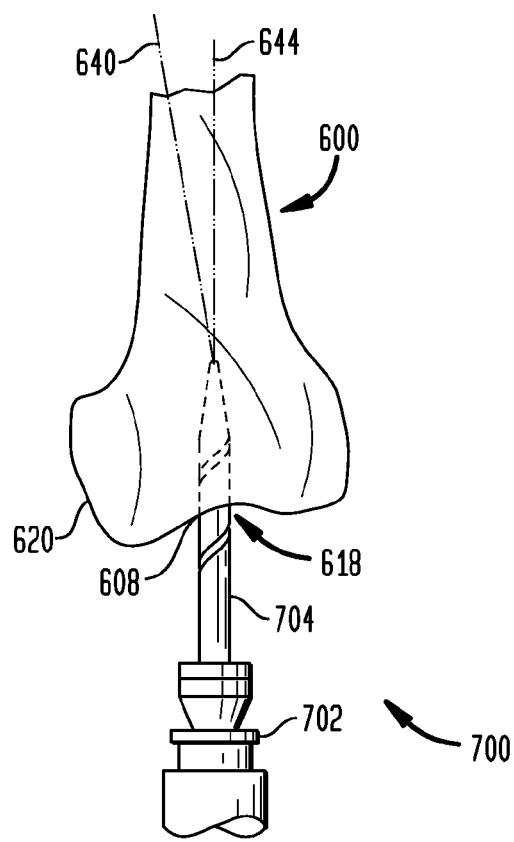
FIG. 19 shows another view of the femur bone of FIG. 18 with the entrance hole being formed.
Figure 20:
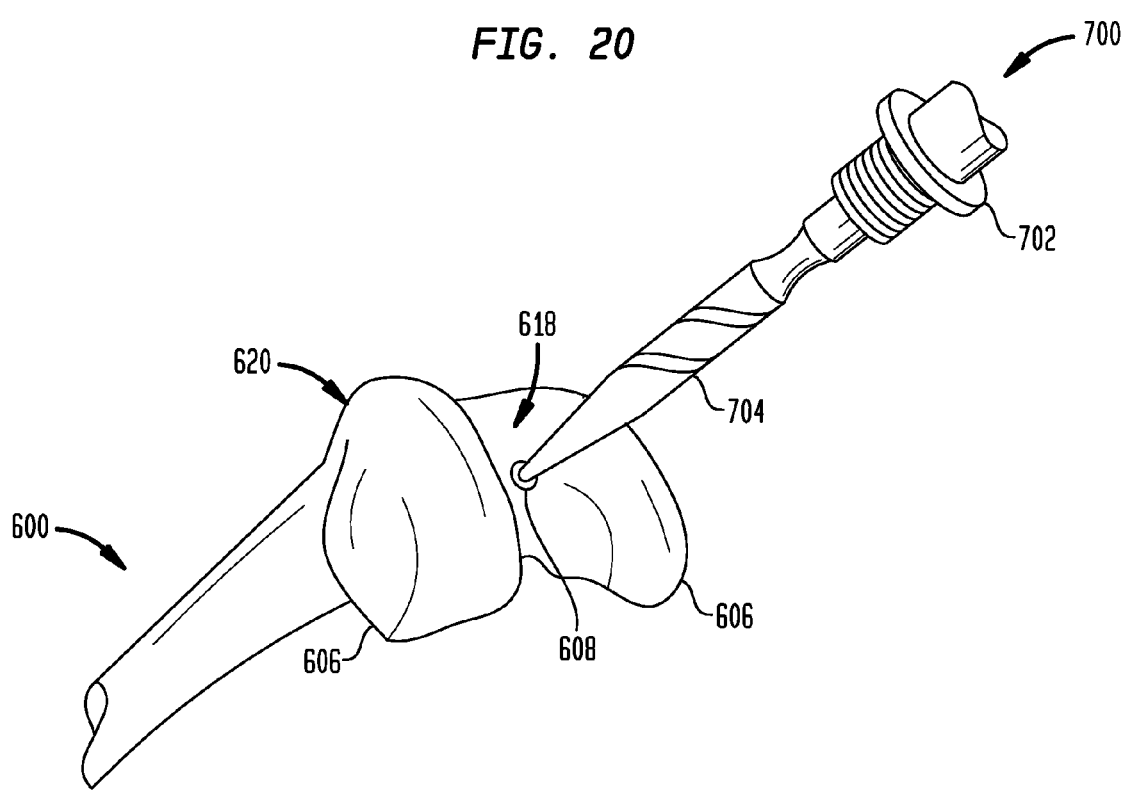
FIG. 20 shows another view of the femur bone of FIG. 19.

FIGS. 19 and 20 show the next step in the surgical procedure which includes the formation of the entrance hole 608 in the distal femur 620. Once the location has been determined of where the entrance hole 608 is to be made, as explained above, the entrance hole 608 can then be formed. This includes using a drill device 700 comprising a drill bit 704 attached to a drill handle 702 (partially shown) well known in the art. Once the drill device 700 is assembled, the free end of the drill 704 is placed against the distal femur at the location at which the entrance hole 608 is to be made. The femur 600 has a mechanical axis 640 and an anatomical axis 644 which is offset from the mechanical axis 640 by approximately 7 degrees. The drill 704 is aligned with the anatomical axis 644. The drill device 700 is then advanced into the location of the entrance hole 608 and manipulated to create the entrance hole 608. As explained below, the femoral medulla can be formed using drill device 700 except with a different drill adapted to make the femoral medulla, as explained below in detail.

Figure 21:
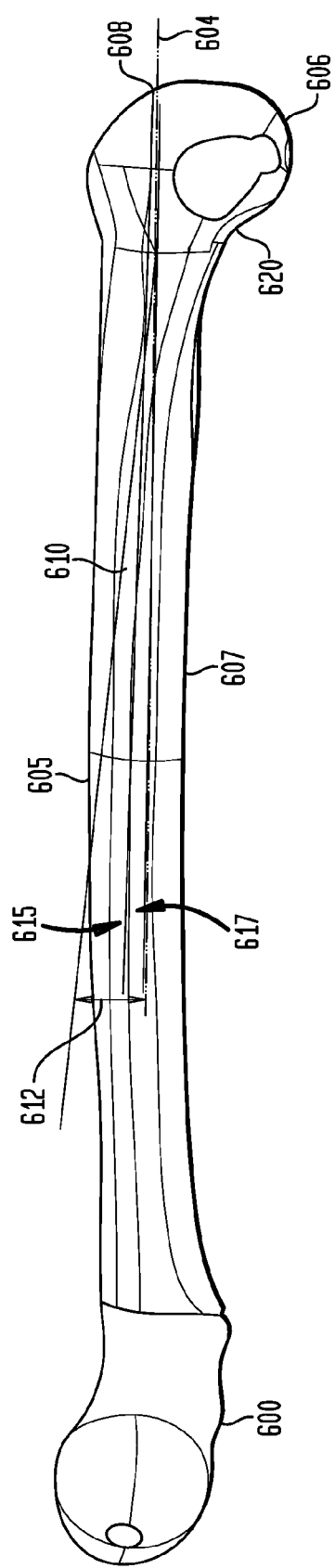
FIG. 21 shows a femoral medulla of a femur bone formed along a plane parallel to the sagittal plane.
Figure 22:
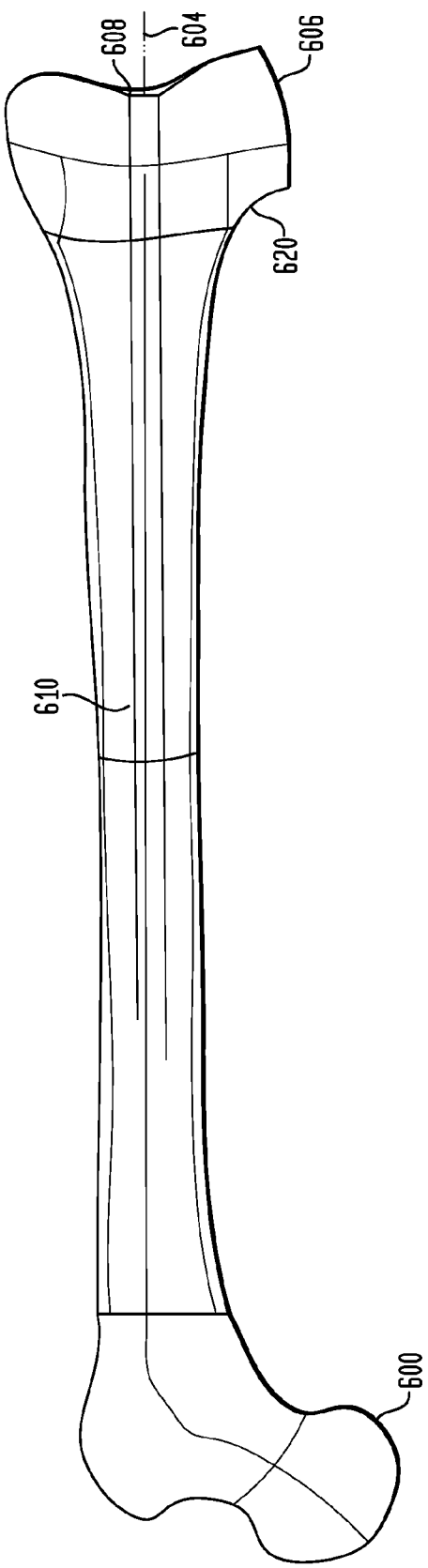
FIG. 22 shows the bone of FIG. 21 along the coronal plane.

Referring to FIGS. 21 and 22, the next step in the surgical procedure involves enlarging the femoral medulla 610 in the femur bone. FIG. 21 shows a cutaway view of the femur bone 600 along a plane parallel to the sagittal plane and FIG. 22 shows a cutaway view of the femur bone 600 along the coronal plane. The bone 600 has an anterior side 605 facing closer to the anterior surface of a human body and a posterior side 607 facing closer to a posterior surface of a human body. As explained above, the drill device can be used to form the entrance hole 608. Once the entrance hole 608 is formed, a drill (reamer) device, such as drill device 700 with an appropriate drill for forming the femoral medulla (FIG. 20), can be used to form femoral medulla 610. The femoral medulla 610 can be formed as a canal through a portion of the interior of the bone sufficient to accommodate the length of the rod. FIG. 22 shows the bone 600 along the coronal plane with a vertical axis 604 drawn perpendicular to the distal end 620 of the femur which extends through the center of the bone 600 and is aligned with the center of the femoral medulla 610. FIG. 21 shows the bone 600 along a plane parallel to the sagittal plane with the femoral medulla 610 having an anterior bone cortex 615 and a posterior bone cortex 617. The center of the femoral medulla 610 is offset from the vertical axis 604 in a radius in the range from about 0 degrees to about 9 degrees shown by arrow 612. In other words, the femoral medulla 610 bows or bends toward the posterior side 607 of the bone along a plane parallel to the sagittal plane but remains relatively straight along the coronal plane. As explained below, the rod of the present invention, when inserted in the femoral medulla, conforms to the bow of the femoral medulla along a plane parallel to the sagittal plane and remains relatively straight along the coronal plane.

Figure 23:
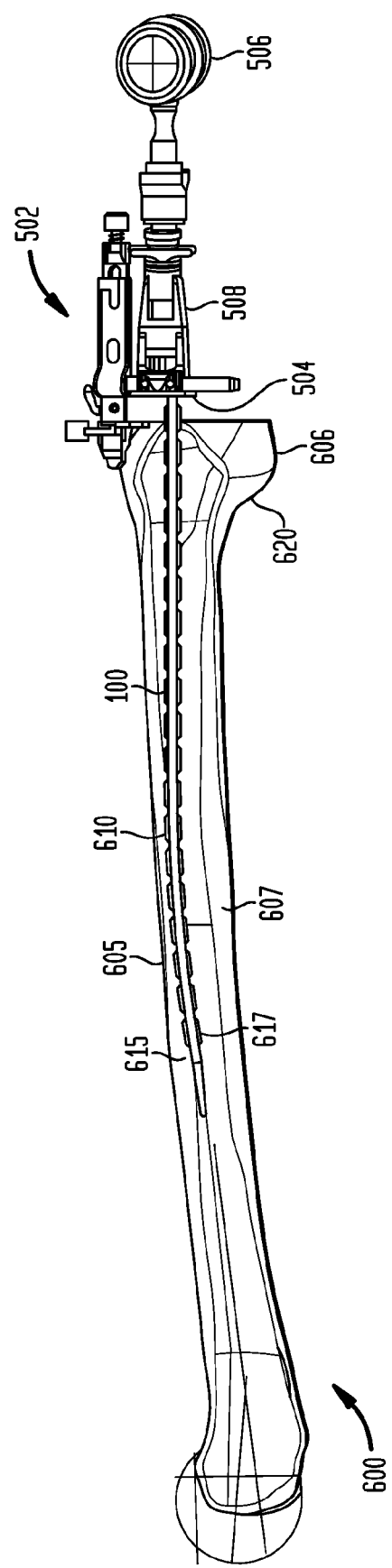
FIG. 23 shows the rod of the kit of FIG. 17 being inserted in the bone of FIG. 21 along a plane parallel to the sagittal plane.
Figure 24:
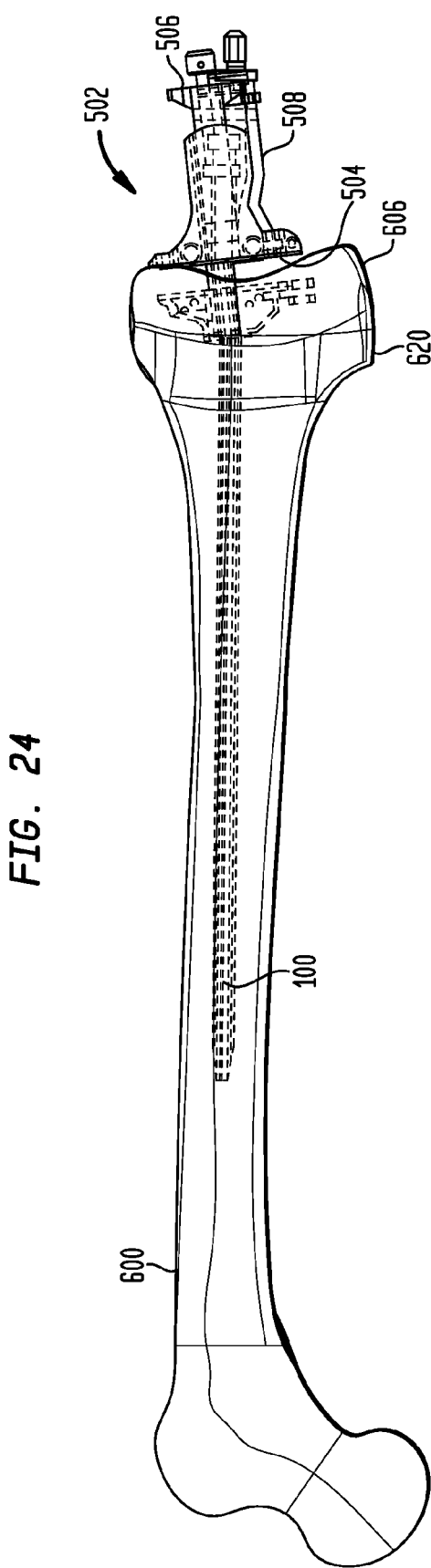
FIG. 24 is a view of the bone of FIG. 23 along the coronal plane.
Figure 25:
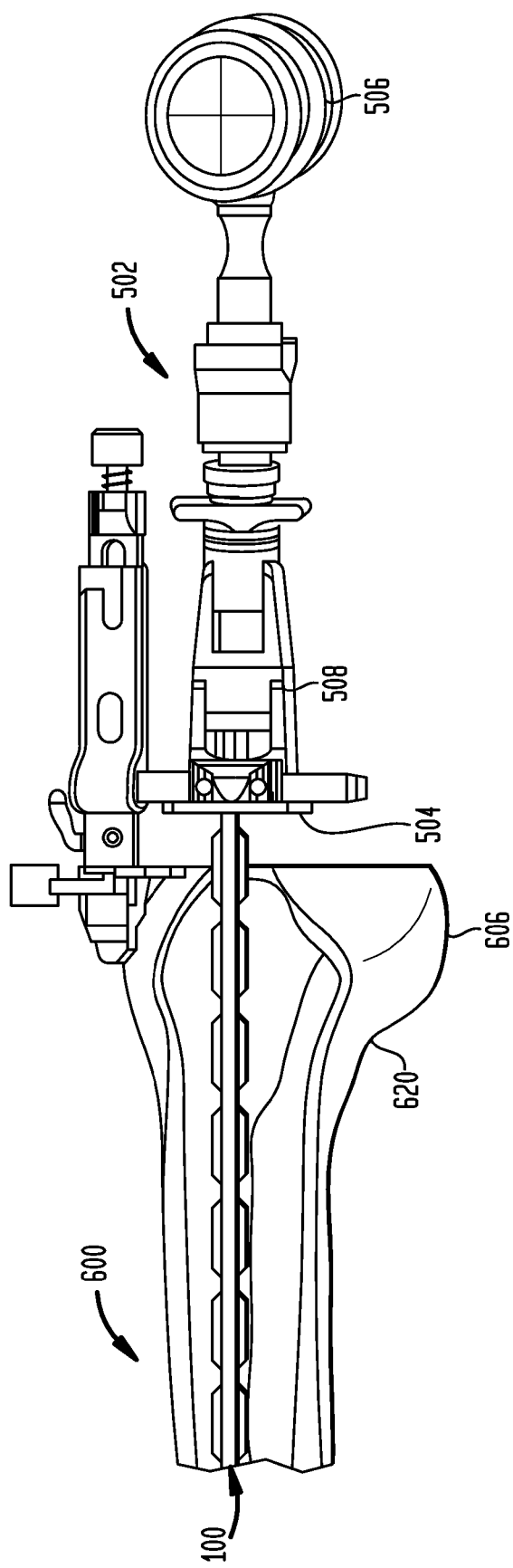
FIG. 25 shows a close up view of FIG. 24.

Turning to FIGS. 23-25, the next step in the surgical procedure involves inserting the rod 100 into the femoral medulla 610. This includes using the surgical kit 500 of FIG. 17 to insert the rod 100 into the femoral medulla 610. For example, in one embodiment, the attachment portion 119 at the second end 118 of the rod 100 can be attached to the attachment portion 504 of the tool 502. Once the tool 502 is properly attached to the rod 100, the rod can be aligned within the femoral medulla 610 such that the anterior portion 105 of the rod faces the anterior bone cortex 615 of the femoral medulla 610 and the posterior portion 107 of the rod faces the posterior bone cortex 617. This alignment helps the rod to be easily inserted into the femoral medulla with relatively little resistance. As explained above, the rod 100 is adapted to flex along a plane parallel to the sagittal plane and conform to the bow of the femoral medulla 610.

Once the rod 100 is aligned with the femoral medulla 610, the rod 100 can be inserted into the femoral medulla 610 using the tool 502. In one embodiment, this can be accomplished by applying a force to one end of the handle 506 of the tool and urging the tool 502 towards the femoral medulla 610 thereby inserting the rod 102 into the femoral medulla. The handle 506 can be rotated about axis 604 to orient the rod according to a particular angle. As the rod enters the femoral medulla 610, the anterior bone cortex 615 of the femoral medulla 610 contacts the anterior portion 105 of the rod causing the rod to flex along a plane parallel to the sagittal plane and conform to the bow of the femoral medulla 610.

Figure 26:
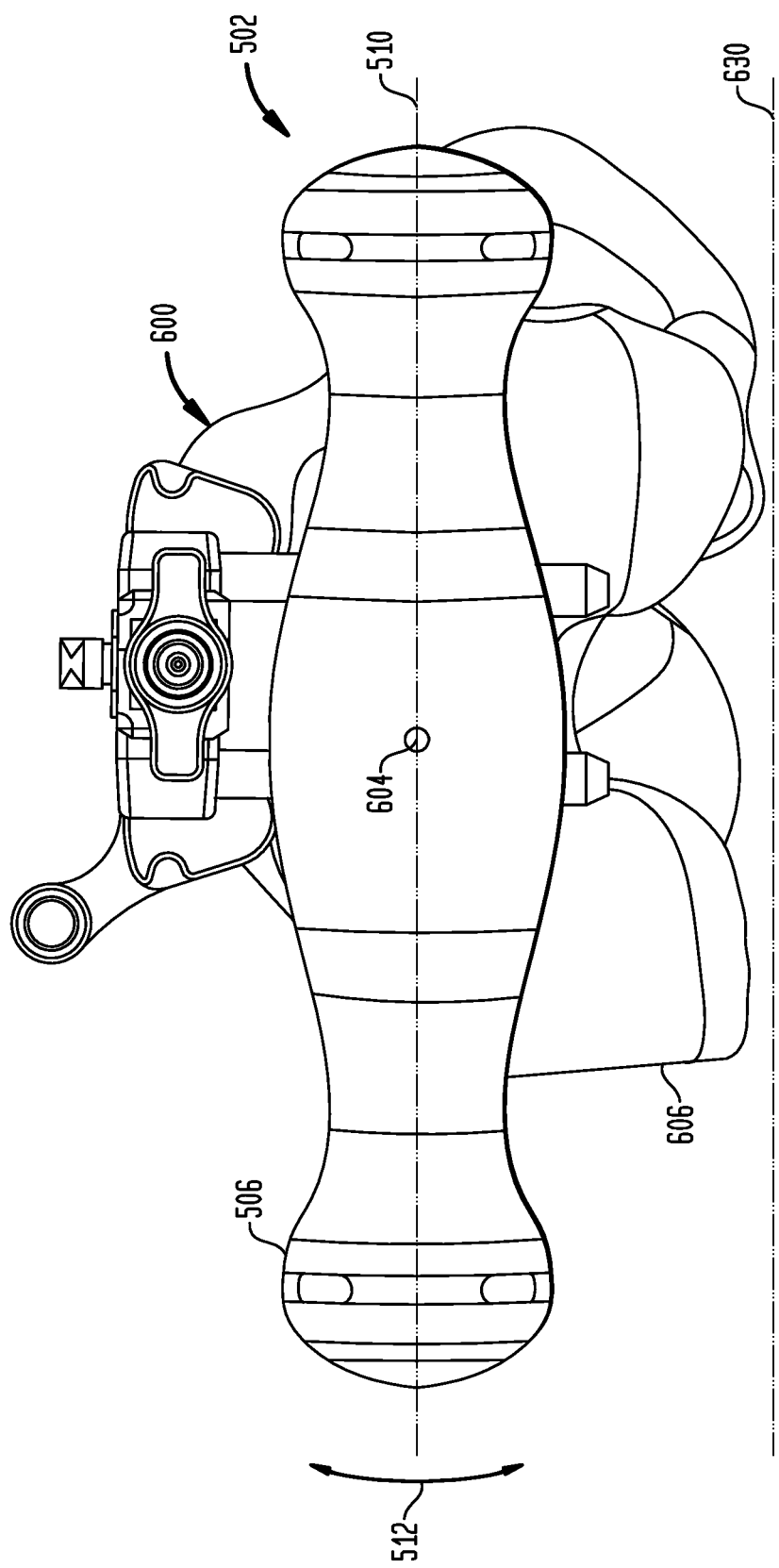
FIG. 26 shows the adjustment of the rod in the bone of FIG. 25.
Figure 27:
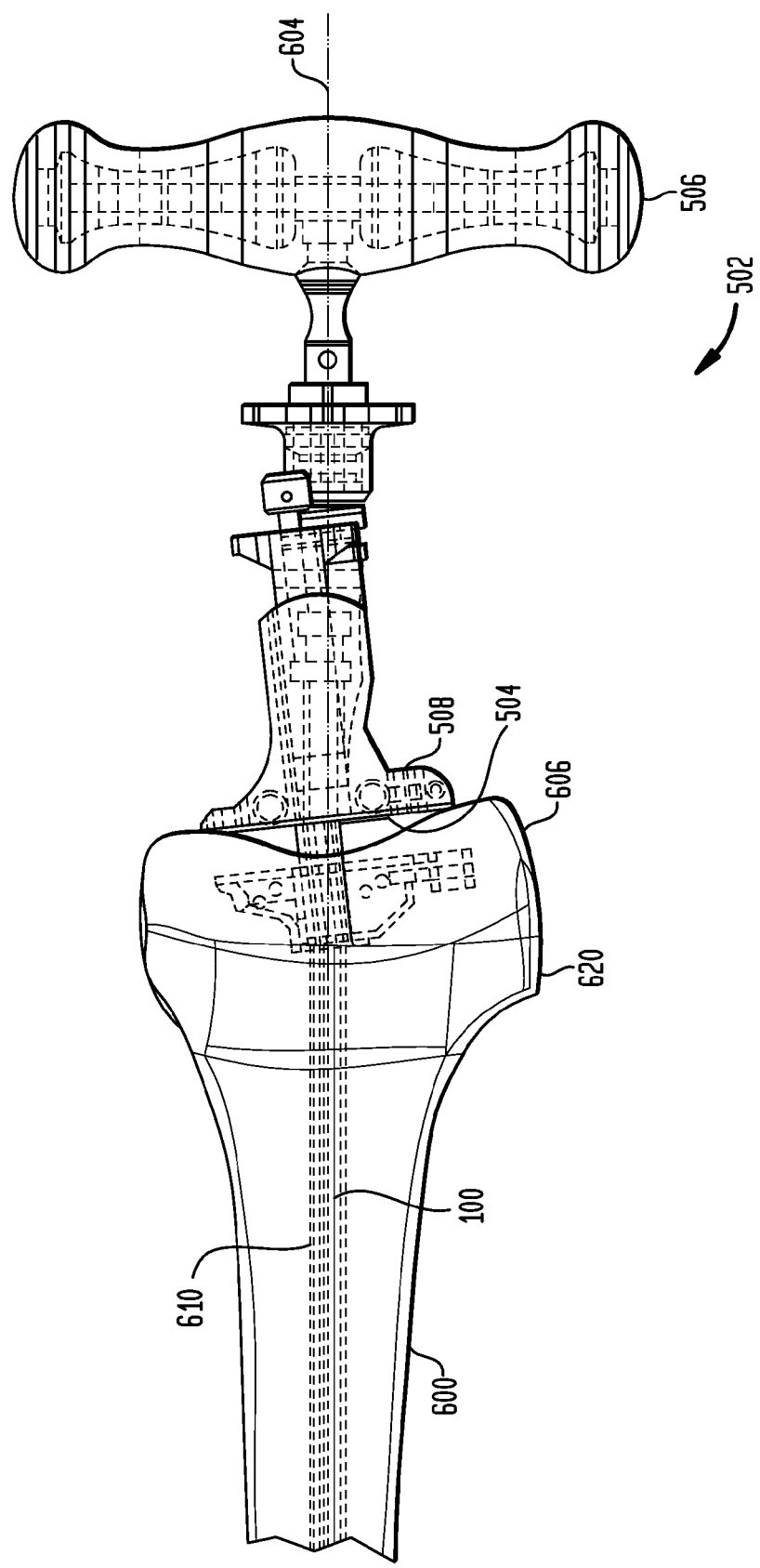
FIG. 27 is another view of FIG. 26.

Turning to FIGS. 26 and 27, the next step in the procedure involves aligning the rod with respect to the femoral medulla 610. Referring to FIG. 26, this alignment can include adjusting the position of the rod along a plane parallel to the sagittal plane. In one embodiment, the handle can be rotated about the axis 604 in the direction shown by arrow 512. The handle is rotated in a manner to orientate a longitudinal axis 510 of the handle 506 with the condyles 606 such that the handle 506 is arranged approximately parallel to an axis 630 of the condyles. In this regard, the handle 506 and the condyles 606 are arranged approximately perpendicular to the bow of the femoral medulla 610 and parallel to the coronal plane.

The position of the rod can also be adjusted along the coronal plane, as shown in FIG. 27. In one embodiment, the rod can be adjusted to establish an appropriate valgus/varus angle with respect to the distal femur along the coronal plane. In one embodiment, the alignment guide 508 can be used for either the left or right femur and can be set to angles between 2 and 9 degrees of the valgus. In one embodiment, the angle is set to a value between 5 and 7 degrees. The alignment guide 508 is set to a particular angle by pulling back on an adjustment knob and placing it onto an appropriate notch of the guide. The alignment guide 508 can then be advanced, along with the rod which is attached thereto, slowly into in the femoral medulla until a desired depth of the femoral medulla has been reached. This ensures that the alignment guide 508 is flush against a prominent condyle. In addition, the handle 506 can be aligned with the condyles as explained above.

Figure 28:
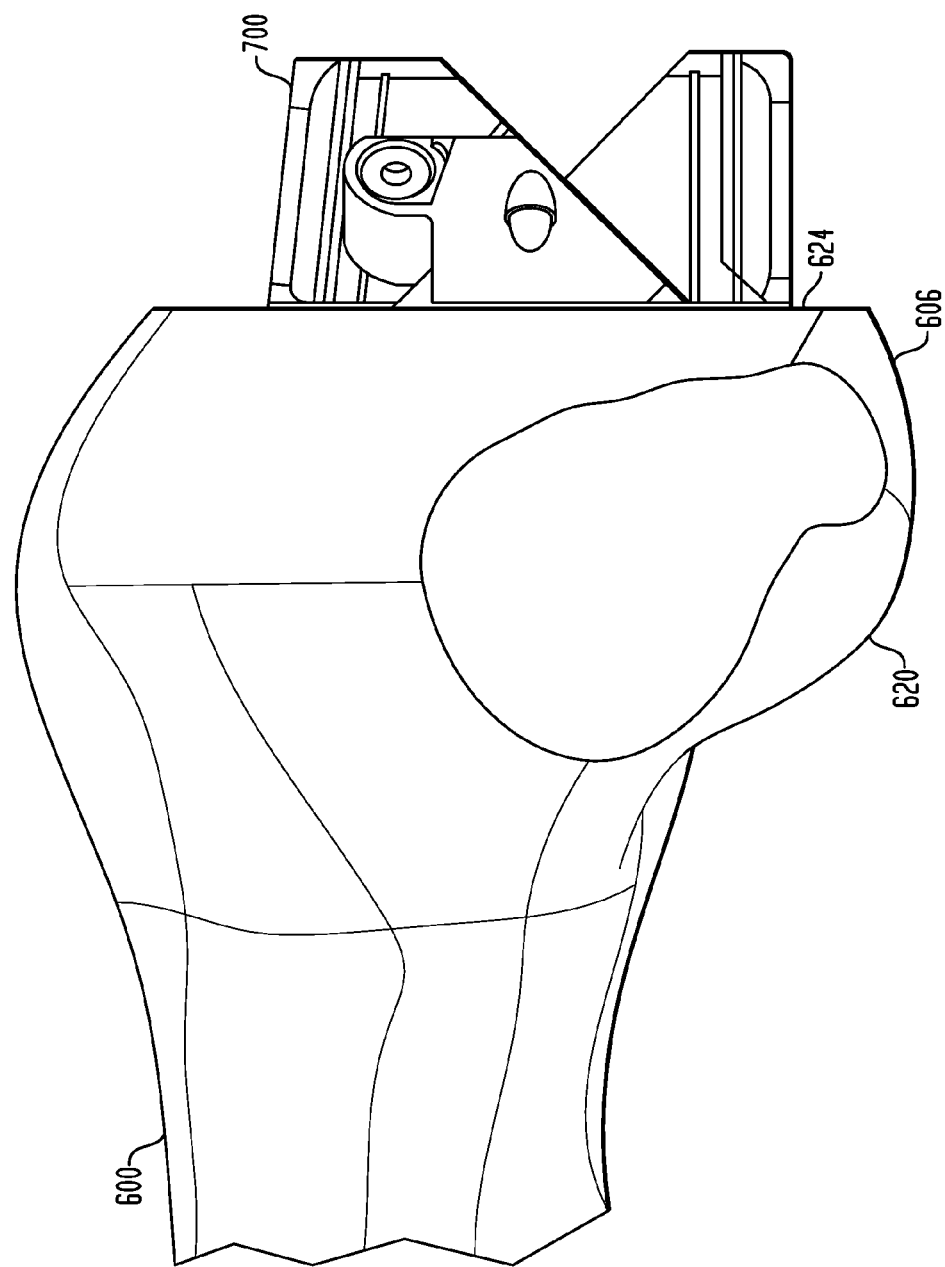
FIG. 28 shows a view of the bone of FIG. 25 with a cutting block attached to the rod.

Turning to FIG. 28, the next step in the surgical procedure includes making the cuts to the distal femur. In one embodiment, this process includes the step of detaching the tool 502 from the rod 102 and leaving the rod inserted in the femoral medulla 610. Once the tool has been detached, a cutting block 700 is mounted onto the rod 102 and placed against the distal surface 624 of the distal femur 620. The rod 100 is oriented to provide a reference for making the cuts to the distal femur 620 including the distal cut. The resection or cuts are made in a manner to accommodate the knee prosthesis. Once the cuts are made, the knee prosthesis (not shown) can be mounted onto the distal surface 624 of the distal femur using conventional techniques.

In another embodiment, an IM instrumentation technique can be used for orienting femoral components in the sagittal plane. The technique includes a step of forming the entrance hole 608 as close as possible to a posterior cruciate ligament (PCL) (not shown) point at the distal femur 620 as possible. In a subsequent step, a rod such as rod 100 can be inserted into the entrance hole 608 and into the medulla 610. As explained above, the rod is flexible along a plane parallel to the sagittal plane and relatively rigid in the coronal plane which establishes an appropriate varus/valgus angle. The rod 100 can be inserted into the hole in a manner such that it is orientated at about three degrees of external rotation with respect to the alignment guide. The technique further includes a step of establishing the valgus angle and distal resection level. Once these are established, the distal cut will be aligned properly and oriented to conform or match the sagittal bow. Once the distal cuts have been made, conventional femoral preparation techniques can be used.

In yet another embodiment, a navigation based technique can be used for orientating femoral components in the sagittal plane. This technique includes a step of using a patient's computed tomography (CT) scan data to determine an optimal sagittal orientation for the femoral component. This may include establishing an orientation of the alignment guide to be offset at an angle with respect to the vertical axis 604 based on the CT data. In a subsequent step, the CT scan data can be used to align the alignment guide in accordance with a predefined angle and then making the distal cuts in accordance with the predefined angle. Once the distal cuts have been made, conventional femoral preparation techniques can be employed.

The techniques of the present invention may provide various advantages. For example, in some embodiments, the configuration of the rod conforms to the bow of the femoral medulla which allows for ease of insertion into the femoral medulla. This may permit the rod to be inserted into the medulla without having to increase the size of the entrance hole during the surgical procedure. In addition, the rod can be inserted without having to shift or enlarge the entrance hole in an anterior direction. Moreover, the entrance hole can be drilled without having to "toggle" the drill device. Such techniques may help reduce the occurrence of deviation of the sagittal plane alignment of the rod and the cutting block which may help improve knee biomechanics. For example, proper orientation of the cutting block may result in correct orientation of the distal cuts, which in turn, determines the orientation of the femoral component such as a knee prosthesis. Such techniques may also improve collateral ligament tension through flexion. In addition, the accuracy of the sizing of the femoral component may help reduce the occurrence of femoral size mismatching the tibial size which may result in improved posterior femoral fit as well as flexion. Such technique may also reduce the occurrence of over-stuffing the patella and reduce the propensity for anterior notching.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A surgical instrument comprising:
an elongated rod having a longitudinal axis disposed on a first plane and a second plane; a plurality of diametrically opposed cutouts formed in at least a portion of a length of the rod and on both proximal and distal portions of the length of the rod along the longitudinal axis, the proximal and distal portions being on separate halves of the rod separated by a transverse plane perpendicular to the longitudinal axis, wherein the cutouts lack communication through the rod, and wherein the rod is flexible along the second plane which is perpendicular to the first plane, the second plane intersecting the cutouts; and one or more grooves each formed in and extending along at least one of the proximal and distal portions of the length of the rod.

2. The surgical instrument of claim 1, wherein the elongated rod is generally solid.

3. The surgical instrument of claim 1, wherein the rod is substantially rigid along the first plane.

4. The surgical instrument of claim 3, wherein the rod is resiliently flexible along the second plane to an angle in the range of about 0 degrees to about 9 degrees from a mechanically straight position of the rod.

5. The surgical instrument of claim 3, wherein the one or more grooves include at least two grooves on each of opposite sides of the first plane.

6. The surgical instrument of claim 3, wherein at least a portion of the cutouts have a generally flat shape extending in a direction parallel to the longitudinal axis.

7. The surgical instrument of claim 3, wherein the cutouts have a generally semi-circular profile within the second plane.

8. The surgical instrument of claim 3, wherein the rod has a tapered first end adapted for insertion into a canal of a bone and a second end adapted for attachment to a tool to support the rod.

9. The surgical instrument of claim 8, wherein the second end has a generally hexagonal cross-sectional shape.

10. The surgical instrument of claim 3, wherein the elongated rod includes a central core disposed along the longitudinal axis, the central core defining a solid surface of the cutouts.

11. The surgical instrument of claim 3, wherein the one or more grooves are a plurality of grooves, and wherein each of the grooves share a common edge with a cutout.

12. The surgical instrument of claim 3, wherein each of the one or more grooves are located between the first plane and the second plane and extend in a direction perpendicular to the transverse plane.

13. The surgical instrument of claim 12, wherein the one or more grooves include at least a pair of adjacent grooves, wherein the pair of adjacent grooves are offset from each other about the longitudinal axis of the elongated rod by an angle of at least 45 degrees.

14. The surgical instrument of claim 12, wherein each of the one or more grooves extend at least one of proximally beyond the cutouts on the proximal portion of the elongated rod and distally beyond the cutouts on the distal portion of the elongated rod.

15. The surgical instrument of claim 1, wherein the rod includes opposing flat surfaces extending along the proximal and distal portions of the length of the rod.

16. A surgical instrument kit comprising:
the surgical instrument of claim 1; and
a tool having an attachment portion for attachment to an end of the rod, wherein the tool has a handle rotatably coupled to the attachment portion for rotating the rod.

17. A surgical instrument comprising:
a solid elongated rod having a longitudinal axis disposed on a first plane and a second plane, the rod being substantially rigid along the first plane; a plurality of diametrically opposed cutouts formed in at least a portion of a length of the rod and on both proximal and distal portions of the length of the rod along the longitudinal axis, the proximal and distal portions being on separate halves of the rod separated by a transverse plane perpendicular to the longitudinal axis, and wherein the rod is resiliently flexible along the second plane which is perpendicular to the first plane, the second plane intersecting the cutouts; and a plurality of grooves each formed in and extending along at least one of the proximal and distal portions of the length of the rod, at least one of the grooves being on a first side of the first plane and at least the other of the grooves being on a second side of the first plane opposite the first side.

18. The surgical instrument of claim 17, wherein the rod is resiliently flexible along the second plane to an angle in the range of about 0 degrees to about 9 degrees from a mechanically straight position of the rod.

19. The surgical instrument of claim 17, wherein at least a portion of the cutouts have a generally flat shape extending in a direction parallel to the longitudinal axis.

20. The surgical instrument of claim 17, wherein each of the grooves share a common edge with a cutout.

21. The surgical instrument of claim 17, wherein each of the grooves are located between the first plane and the second plane and extend in a direction perpendicular to the transverse plane.

22. The surgical instrument of claim 17, wherein the plurality of grooves include at least a pair of adjacent grooves, wherein the pair of adjacent grooves are offset from each other by an angle of at least 45 degrees.

23. The surgical instrument of claim 22, wherein each of the plurality of grooves extend at least one of proximally beyond the cutouts on the proximal portion of the elongated rod and distally beyond the cutouts on the distal portion of the elongated rod.

24. The surgical instrument of claim 17, wherein the rod includes opposing flat surfaces extending along the proximal and distal portions of the length of the rod.

25. A surgical instrument comprising:
a solid elongated rod having a longitudinal axis disposed on a first plane and a second plane, the rod being substantially rigid along the first plane; a plurality of diametrically opposed cutouts formed in at least a portion of a length of the rod and on both proximal and distal portions of the length of the rod, the proximal and distal portions being separated by a transverse plane perpendicular to the longitudinal axis, wherein the rod is resiliently flexible along the second plane which is perpendicular to the first plane, the second plane intersecting the cutouts and the rod being resiliently flexible along the second plane to an angle in the range of about 0 degrees to about 9 degrees from a mechanically straight position of the rod, and wherein the cutouts have a generally semi-circular profile within the second plane; and a plurality of grooves each formed in and extending along both the proximal and distal portions of the length of the rod, at least one of the grooves being on a first side of the first plane and at least the other of the grooves being on a second side of the first plane opposite the first side, wherein each of the grooves share a common edge with a cutout, and wherein each of the grooves are located between the first plane and the second plane and extend in a direction perpendicular to the transverse plane.

26. The surgical instrument of claim 25, wherein at least a portion of the cutouts have a generally flat shape extending in a direction parallel to the longitudinal axis.

27. The surgical instrument of claim 25, wherein the plurality of grooves include at least a pair of adjacent grooves, wherein the pair of adjacent grooves are offset from each other by an angle of at least 45 degrees.

28. The surgical instrument of claim 27, wherein each of the plurality of grooves extend at least one of proximally beyond either the cutouts on the proximal portion of the elongated rod and distally beyond the cutouts on the distal portion of the elongated rod.

29. The surgical instrument of claim 25, wherein the rod includes opposing flat surfaces extending along the proximal and distal portions of the length of the rod.

* * * * *